United States Patent [19]

Golstein

[11] 4,210,429
[45] Jul. 1, 1980

[54] AIR PURIFIER

[75] Inventor: Jerome J. Golstein, Denver, Colo.

[73] Assignee: Alpine Roomaire Systems, Inc., Denver, Colo.

[21] Appl. No.: 936,736

[22] Filed: Aug. 25, 1978

Related U.S. Application Data

[63] Continuation of Ser. No. 784,157, Apr. 4, 1977, abandoned.

[51] Int. Cl.² .......................................... B01D 46/10
[52] U.S. Cl. ....................................... 55/279; 55/473; 422/24; 422/121
[58] Field of Search ............... 55/279, 473; 422/24, 422/121

[56] References Cited

U.S. PATENT DOCUMENTS

| | | | |
|---|---|---|---|
| 2,248,618 | 7/1941 | Fischer | 422/24 |
| 2,449,681 | 9/1948 | Wilson | 21/74 R |
| 2,553,711 | 5/1951 | Jackson | 55/279 |
| 2,628,083 | 2/1953 | Reuse | 55/279 |
| 2,945,554 | 7/1960 | Berly | 55/279 |
| 3,576,593 | 4/1971 | Cicirello | 55/279 |
| 3,757,495 | 9/1973 | Sievers | 55/472 |
| 3,812,370 | 5/1974 | LaViolette | 55/473 |
| 3,935,803 | 2/1976 | Bush | 55/473 |

FOREIGN PATENT DOCUMENTS 856169 12/1960 United Kingdom ................. 55/103

Primary Examiner—Frank Sever
Attorney, Agent, or Firm—Wolf, Greenfield & Sacks

[57] ABSTRACT

A room air purifier for quietly removing irritating or harmful impurities from the air circulating within the room. The purifier removes from room air, particles down to 0.3 microns in size with 99.9% efficiency. The air purifier comprises a somewhat elongated upright housing having an easily-removable back, a two-speed blower that is preferably AC operated and disposed at the bottom of the housing, a pair of vertically disposed ultraviolet lamps and associated means for powering the lamps including push button switch means, and preferably three separate filters including a pre-filter disposed at the inlet of the blower, a highly efficient main filter element vertically stacked over the blower and lamps and a charcoal filter disposed over the main filter element. The blower sucks the air in the bottom of the purifier through the pre-filter and up adjacent to the lamps to the main filter element and charcoal filter, and from there the purified air passes to a top baffle cover where the air is exited in preferably four directions from the purifier.

4 Claims, 7 Drawing Figures

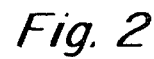
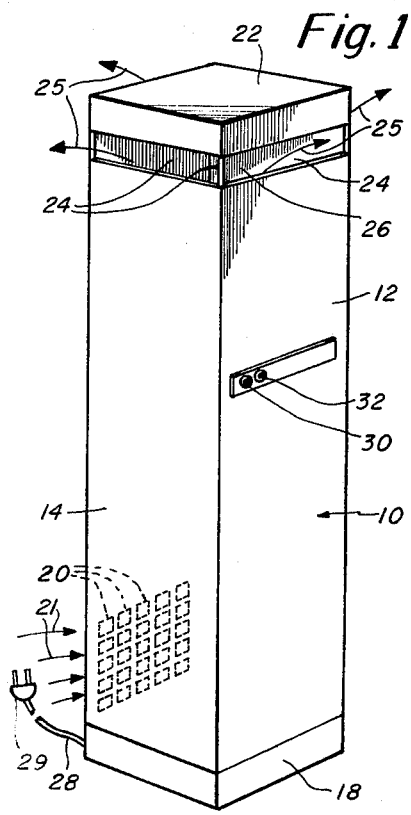
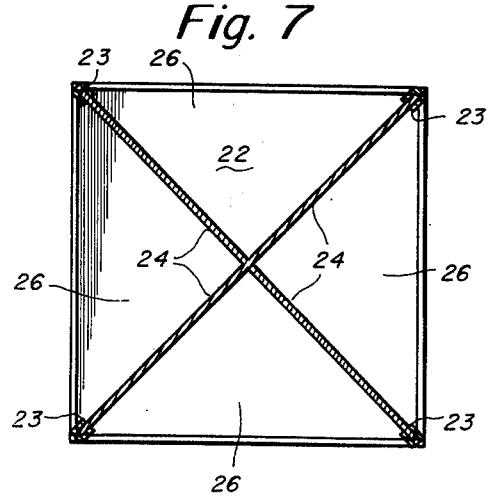
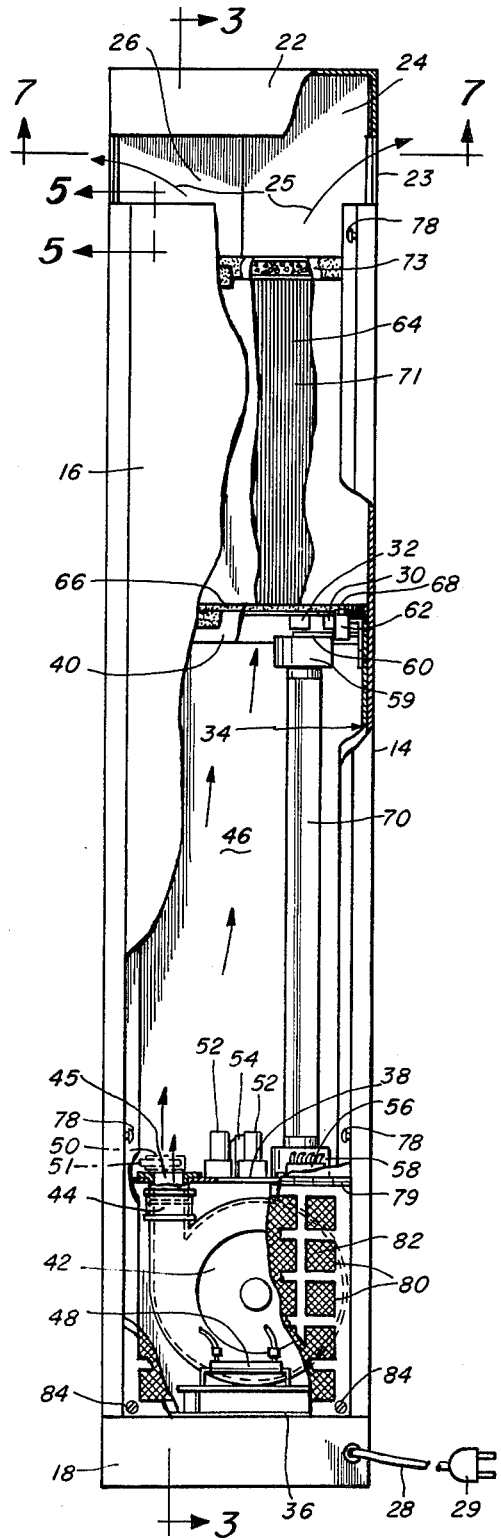

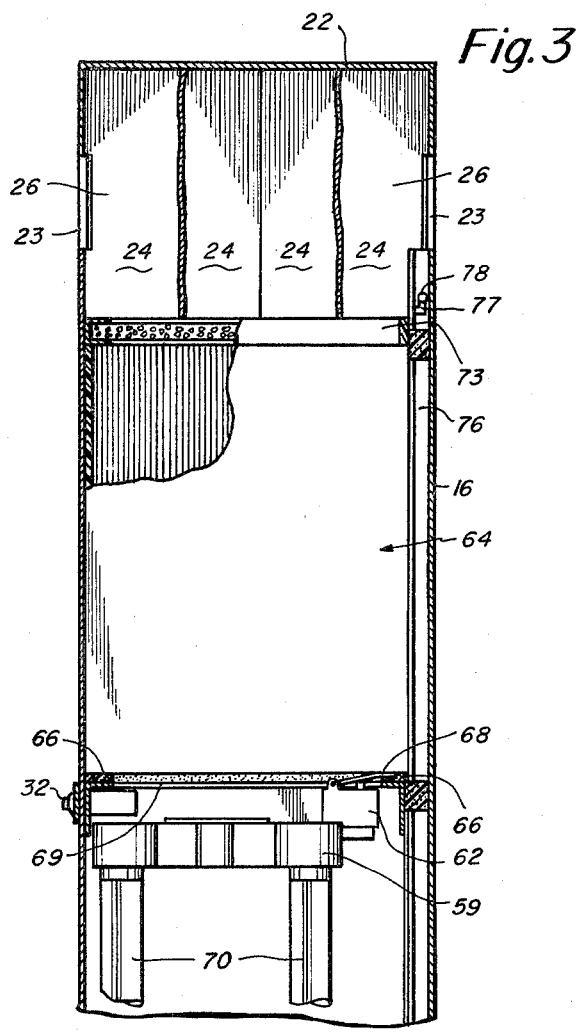
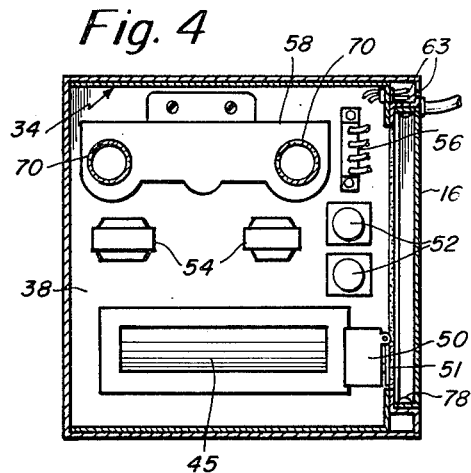
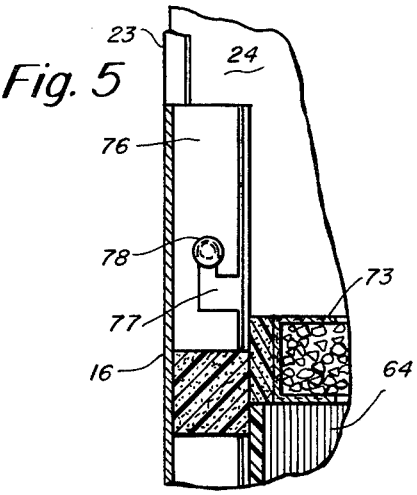
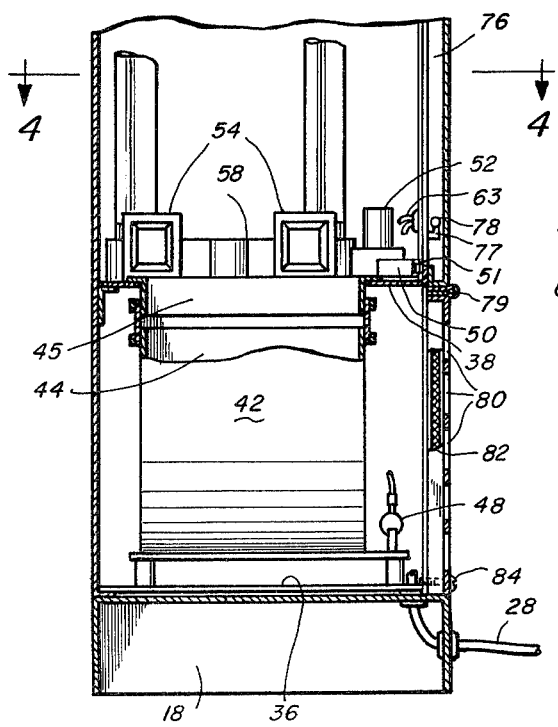
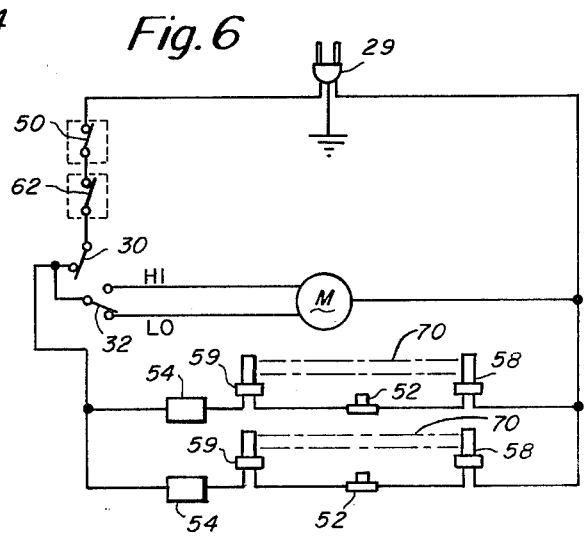

4,210,429

AIR PURIFIER

This is a continuation of application Ser. No. 784,157, filed Apr. 4, 1977 now abandoned.

BACKGROUND OF THE INVENTION

The present invention pertains to an air purifier for removing irritating or harmful impurities from the air. More particularly, in the preferred embodiment of the invention the air purifier is free-standing and is a totally self-contained unit powered solely from a conventional AC source.

Pollens, lung damaging dust, smoke, bacteria and any one of a number of other irritants and micro-organisms are quite likely in the air that everyone breathes. These irritants are carried by the wind, on people's clothing, on the hair or feathers of a pet, or sprayed about by a sneeze or a cough. Contact with these irritants is almost inevitable. Also, for persons plagued by the miseries of emphysema, asthma, hay fever or other allergies, contact with irritants and micro-organisms means unpleasant discomfort and usually sleepless nights. Although different types of air purifiers presently exist, they are not completely effective in removing these irritants and micro-organisms from the air. Further, existing air purifiers do not provide the combination of effective removal of these contaminants along with the provision of a germicidal chamber for killing and oxidizing bacteria and virus.

Accordingly, an object of the present invention is to provide an improved air purifier that has an improved filtration efficiency. The purifier of this invention removes from the air particles down to 0.3 micron in size with an efficiency of 99.9%. Unlike the electro-static type filters used in some purifiers the filtration system of the present purifier maintains this high filtration efficiency for a considerable length of time.

Another object of the present invention is to provide an air purifier having a plurality of filters comprising the filtration system including a main filter, a filter for removing offensive odors and a pre-filter for filtering the larger particles from the air and in this way increasing the efficient light span of the main filter.

Still another object of the present invention is to provide an air purifier having, in addition to the efficient filtration system, an ultraviolet bacteria killing system employing preferably two ultraviolet lamps for killing and oxidizing bacteria and virus.

Still another object of the present invention is to provide an air purifier wherein the components of the purifier are generally stacked in a vertical fashion within an elongated upright housing with the air being passed through the housing in a generally vertical upward direction. The air purifier of this invention draws air in at floor level and discharged preferably in four directions to provide optimum mixing of air in the room and as the air is discharged it filters down the bottom of the room where it is recirculated. As it filters down, it gathers particulates, providing optimum efficiency for the purifier.

Another object of the present invention is to provide preferably a pair of ultraviolet lamps which are arranged also in a vertical fashion within the housing of the air purifier so that the particles to be collected travel the length of the lamp thereby getting more exposure than if they traveled in another direction with relationship to the lamps.

A further object of the present invention is to provide a room air purifier which is useable in bedrooms, living rooms, offices, conference rooms, lounges, waiting rooms and any place where people with allergies or respiratory problems may be.

Still another object of the present invention is to provide an air purifier that is compact, quiet, and attractive, requiring no special installation, and that is easy to move from room to room if necessary.

A further object of the present invention is to provide an air purifier having a two-speed blower and preferably two switches, one of which is an on-off switch and the other of which is a high-low blower speed switch.

A further object of the present invention is to provide safety interlock switches associated with the air purifier for preventing exposure to the ultraviolet lamps should the housing be opened while the air purifier is operating.

SUMMARY OF THE INVENTION

To accomplish the foregoing and other objects of the invention the air purifier comprises a somewhat elongated upright housing including a base, preferably four upright rigid walls, including a removable back wall, and a top cover. In the disclosed embodiment the air enters the housing through an opening in the removable back wall and the top cover defines four outlets through which the purified air exits. The blower means is disposed at the bottom end of the housing for drawing air into the housing through the opening in the back wall of the housing. The blower means is preferably a two-speed blower and operates from a conventional 110 volt AC line. The control buttons for operating the purifier including an on-off push button, and a high-low push button for selectively operating the blower at either high or low speed. There is a germicidal chamber defined within the housing and containing preferably a pair of ultraviolet lamps which are disposed within this chamber for killing bacteria flowing through the chamber. The germicidal chamber is disposed above the blower means and filter means are provided in the housing above the germicidal chamber. This filter means preferably includes a main filter and a charcoal filter disposed above the main filter. The main filter is a special high efficiency filter referred to in the trade as a Hepa filter. A third filter is also preferably used and this is a pre-filter disposed in the inlet opening of the housing for pre-filtering the larger particles prior to them flowing into the germicidal chamber by way of the blower means. To prevent exposure to the ultraviolet lamps there are provided preferably a pair of interlock switches. One of the interlock switches interrupts power when the back panel of the housing is removed and the other interlock switch interrupts power when the main filter is withdrawn to the top of the housing.

DESCRIPTION OF THE DRAWINGS

Numerous other objects, features and advantages of the invention should now become apparent upon a reading of the following detailed description taken in conjunction with the accompanying drawings, in which:

FIG. 1 is a perspective view of a preferred embodiment of the air purifier of this invention;

FIG. 2 is a rear elevation of the air purifier shown in FIG. 1 with the back wall partially broken away;

FIG. 3 is a cross-sectional view taken along line 3—3 of FIG. 2;

FIG. 4 is a cross-sectional view taken along line 4—4 of FIG. 2;

FIG. 5 is a fragmentary cross-sectional view taken along line 5—5 of FIG. 2; and FIG. 6 is a schematic diagram associated with the air purifier of this invention.

FIG. 7 is a section plan view of the upper portion of FIG. 2.

FIG. 1 is a perspective view of a preferred embodiment of the air purifier of this invention. The purifier comprises a housing 10 including a front wall 12, a pair of side walls 14, and a removeable rear wall 16. These walls are suitably supported from a base 18. FIG. 1 shows in dotted the inlet 20 to the housing. This inlet is in the back wall and the precise construction is discussed in more detail hereinafter with reference to FIG. 2. The top of the housing 10 is covered by a cover 22 having four radially arranged legs 24 defining four outlets 26 directed in opposite orthogonal directions. The arrows 21 depict the direction of flow of the inlet air while the arrows 25 depict the direction of flow of the outlet air. FIG. 1 also shows the electrical cord 28 and associated plug 29 for connection to a conventional 110 volt AC outlet. In the preferred construction, the housing is 9½ inches square and approximately 50 inches tall. Essentially the only controls for the purifier are shown in FIG. 1 on the front wall 12 and include two-position switch 30 which is an on-off switch and two-position switch 32 which is a highlow switch for controlling blower speed. Both of the switches 30 and 32 are push-to-light switches. When the unit is on and operating, the switch 30 has its red light illuminated. If the switch 32 is also illuminated, it means that the blower is on high speed. To revert to low speed, switch 32 is simply depressed at which time the light goes out indicating that the system is in low blower speed operation.

Referring now to FIGS. 2-5, there is provided a frame 34 which is open at the back and which is dimensioned to slide fit within the housing. The frame 34 has a base plate 36, an intermediate support plate 38, and a top peripheral flange 40. The frame 34 is suitably secured such as by screws to the base 18 once the frame is properly positioned within the housing. The base plate 36 is primarily for supporting the conventional blower 42. The blower 42 has an output duct 44 through which the air is discharged through an opening 45 provided in the intermediate support plate of the frame. The air passes to the germicidal chamber 46 defined between the intermediate plate 48 and the peripheral flange 40. The blower 42 may be one sold by Revcor, Inc. of Carpentersville, Illinois and covered by U.S. Pat. No. 2,915,240. A high ohmage resistor 48 is suitably supported adjacent to the blower 42. This resistor may be a 100 watt 25 ohm resistor and is for dropping the voltage level to the blower.

There are a number of components secured to the intermediate support plate 38 including interlock switch 50, lamp starters 52, lamp ballasts 54, terminal connector 56, and one of the lamp socket assemblies 58. Wiring connects from the terminal connector 56 to the electrical components shown in FIG. 4. Reference is made hereinafter to the schematic diagram of FIG. 6 for a complete description of the wiring associated with these components. The ballasts and the lamp assemblies are conventional items sold by General Electric. For example, the ballast may be a General Electric ballast catalog No. 6G1042. The starters may each be of the type manufactured by Dura Electric Lamp Company Inc. of Newark, New Jersey. These starters are identified by part No. FS-2 and include a lifelong ceramic condensor.

The oppositely arranged lamp socket assembly 59 is secured by means of a bracket 60 from one wall of the frame 34. A second interlock switch 62 is also provided suitably supported from the frame just below the peripheral flange 40. The terminal ends of each of the switches 30 and 32 extend into the housing and wiring is provided from these switches and from the switch 62 as shown by the wires 63 in FIG. 4 coupling down to the terminal connector 56 also shown in FIG. 4.

The main filter 64 has a square cross-section and fits within the housing with its bottom edge resting upon a sponge or foam bumper 66 which may be suitably secured such as by gluing to the top surface of the peripheral flange 40. The in-place position of the filter 64 is sensed by the switch 62 which has a flexible contact 68 which may be depressed by the bottom edge 69 of the filter 64. The leaf 68 of the spring when depressed rests between the edge 69 and the foam bumper 66. The switch 62 as well as the switch 50 is of conventional design. Both of these switches are normally open until the leaf or contact associated therewith is depressed thus closing the switch and permitting power to couple therethrough.

The lamps 70 are suitably supported on conventional spring loaded assemblies at either end. Each of these spring loaded assemblies comprise a part of the conventional lamp socket assembly 58. Each of the lamps 70 are ultraviolet lamps identified by the General Electric part No. G15T8. These lamps are 15 watt germicidal lamps.

The main filter 64 is a known filter element that may be purchased from Hepa Corporation of 3071 East Coronado Street, Anaheim, California. This filter is identified as their model number 100HFR. This filter comprises a plurality of corrugated foil sheets 71 and a special cross membrane. This filter is of the type invented by the Atomic Energy Commission and although other conventional types of main filters could be substituted, this filter is the preferred filter for use in this purifier. It is the main filter that is primarily responsible for removing especially the very small particles with an efficiency of 99.9% of those particles 0.3 microns and larger in size.

A conventional charcoal filter 73 is disposed above the main filter 64. The charcoal or carbon filter 73 is used primarily for removing odors from the air.

The cover 22 simply rests on top of the housing 10. Spacers 23 are provided clipped to the edges of each of the legs 24 for elevating the cover above the housing and thus providing the outlet ports 26.

Access to the inside of the housing is provided primarily by making the back wall or back panel 16 removeable. FIG. 4 shows the back wall 16 in position secured with the rest of the housing. FIG. 5 shows a fragmentary view of the wall 16 with its inturned lip 76. At two locations on both sides of the panel the lip 76 is slotted as shown in FIG. 5 at 77 to receive adjustable studs 78 which extend from the housing. It can be seen from FIG. 5 by simply raising the back panel a slight distance it can be pulled forwardly and disengage from the rest of the housing. The back wall is essentially constructed in two-pieces including a top piece and a bottom piece interconnected by a hinge 78. The bottom piece thus pivots from the top piece about the hinge 78 and is provided with a plurality of small openings 80. A prefilter 82 is disposed just inside the bottom section of the back wall 16 and the openings 80 provide access through the filter 82 to the inlet of the blower 42. The hinged bottom section of the rear wall is secured in place by means of a pair of screws 84.

As indicated in FIG. 3 there is provided a switch 50 suitably mounted from the intermediate support plate 38. This switch 50 is of conventional design and includes a leaf or contact 51 which is pressed to close the switch when the rear panel 16 is in place. The switch 50 is normally open and thus when the panel is removed the contact 51 moves to open the switch so as to interrupt power to the ultraviolet lamps.

The prefilter 82 may be a conventional fiberglass filter which may be easily replaced by removing the screws 84 and hinging the bottom panel so as to permit removal of this filter. This filter is primarily used for filtering larger particles. This filter is preferably replaced after about 60 days of use. After the prefiltering the blower forces the air into the chamber 46 where the air is subjected to the ultraviolet radiation from the lamps 70. These lamps are oriented vertically as shown because in that way the particles travel along the length of the entire lamp and thus obtain the maximum exposure. The ultraviolet radiation is primarily used for killing viruses and bacteria. For example, asthmatics are prone to upper respiratory infections. Some of the drugs that they use make them more immunosuppressed. The purifier of this invention picks up about 50% of the viruses. However, about 50% are not picked up by the filtration but these are sterilized by the ultraviolet radiation. With the use of these ultraviolet lamps the particles entrapped in the main filter are essentially dead and there is no chance of anything growing in this filter. Bacteria and viruses cannot develop at least for a period of a number of years in the air purifier.

Referring now to FIG. 6 there is shown a schematic diagram of the electrical portion of the air purifier. Essentially all of the components shown in FIG. 6 have been discussed previously with regard to FIGS. 1-5. The power coupled by way of plug 29 couples on one side directly to the blower motor of blower 42. Switches 50 and 62 which are the interlock switches couple in series from the other side of the power line by way of the on-off switch 30 to the mode selection switch 32. In the position shown in FIG. 6 the switches 50 and 62 are closed and the on-off switch 30 is in its on position. This couples power to the switch 32 which in the position shown is coupling operating power to the low input of the blower motor. If switch 32 is depressed to its other position that power is coupled to the high input of the blower motor. As long as the switches 50 and 62 are closed and the switch 30 is also closed, then power is applied to the ultraviolet lamps. This power is shown coupled to the ballast 54, the output of which couples to the lamp sockets 58 and 59 and the starter 52. If either one of the switches 50 or 62 opens because the main filter is removed or the back panel 16 is removed, then all power to the blower motor and the lamps is disconnected. FIG. 7 shows a plan view of FIG. 2, including legs 24.

One of the important features of the present invention is concerned with the general vertical orientation of the components of the purifier. With the present invention the air if drawn in at floor level where particles of air are gravitationally induced, the air is prefiltered, preferably subjected to ultraviolet radiation, and then goes through the main filtering process to be finally discharged preferably in a four-way direction. The air is preferably discharged at essentially eye-level or close to eye level. This is a distinct advantage over prior art units which circulate air only over a relatively short distance. Another important feature of the present invention is the vertical orientation of the ultraviolet lamps permitting maximum exposure of the circulated air.

Having described one embodiment of the present invention it should now become apparent to those skilled in the art that numerous other embodiments are contemplated as falling within the scope of this invention. For example, the unit could possibly be operated from storage batteries rather than from an AC source. Also, many different configurations of blowers can be employed with the invention.

What is claimed is:

1. An air purification system comprising; means defining an elongated upright enclosed housing including a plurality of walls and means forming a base supporting the walls vertically, elongated removable means forming a part of the housing to provide access to the interior of the housing and including a removable panel having a top section and a bottom section hinged from the top section and having a plurality of openings therein; said panel being designed and dimensioned to enable complete disengagement from said housing by only raising said panel a slight vertical distance and polling the bottom thereof outwardly from said housing, a blower disposed at the bottom end of the housing adjacent the bottom section of the removable panel for drawing air into the housing through said plurality of openings in the bottom section, means for selectively operating said blower, a partitioning wall disposed above the blower demarcating the bottom end of the germicidal chamber and having an opening for the blower outlet, means defining a germicidal chamber within the housing having at least one ultraviolet lamp means disposed therein for killing viruses and bacteria flowing through the germicidal chamber, said ultraviolet lamp extending longitudinally of said housing between top and bottom ends of the germicidal chamber with said germicidal chamber having a height at least on the order of the height of the filter, a high efficiency filter disposed in the housing for trapping small particles down to 0.3 microns, flange means on the interior of said housing supporting said filter above said germicidal chamber whereby substantially all viruses and bacteria that are to be destroyed are so destroyed before the air reaches the filter, and means defining an outlet from the top of the housing for discharging the purified air, said housing having a height substantially greater than its width with the filter, blower, and ultraviolet lamp means stacked one above the other, said high efficiency filter dimensioned with a comparable width and depth to those of the housing so as to fit snugly within the housing entirely above the germicidal chamber and ultraviolet lamp means, said blower causing air passage through the germicidal chamber in only one direction past the ultraviolet lamp means.

2. An air purification system as set forth in claim 15 including a prefilter mounted in the housing downstream of the filter and for filtering particles greater than 0.3 microns.

3. An air purification system as set forth in claim 2 including a charcoal filter supported above the main filter.

4. An air purification system as set forth in claim 1 wherein said petitioning wall forms a means for support for one end of the lamp means.

* * * * *